United States Patent
Edelman et al.

(10) Patent No.: US 9,113,810 B2
(45) Date of Patent: Aug. 25, 2015

(54) SYSTEM AND METHOD FOR UNGATED NON-CONTRAST ENHANCED MAGNETIC RESONANCE ANGIOGRAPHY

(71) Applicants: Robert R. Edelman, Highland Park, IL (US); Ioannis Koktzoglou, Des Plaines, IL (US)

(72) Inventors: Robert R. Edelman, Highland Park, IL (US); Ioannis Koktzoglou, Des Plaines, IL (US)

(73) Assignee: NorthShore University Healthsystem, Evanston, IL (US)

( * ) Notice: Subject to any disclaimer, the term of this patent is extended or adjusted under 35 U.S.C. 154(b) by 463 days.

(21) Appl. No.: 13/739,392

(22) Filed: Jan. 11, 2013

(65) Prior Publication Data
US 2014/0200435 A1    Jul. 17, 2014

(51) Int. Cl.
*A61B 5/05* (2006.01)
*A61B 5/055* (2006.01)
*A61B 5/00* (2006.01)
*G01R 33/563* (2006.01)
*G01R 33/565* (2006.01)

(52) U.S. Cl.
CPC ............. *A61B 5/055* (2013.01); *A61B 5/004* (2013.01); *G01R 33/5635* (2013.01); *G01R 33/56509* (2013.01)

(58) Field of Classification Search
CPC .. A61B 5/055; A61B 5/004; G01R 33/56509; G01R 33/5635
USPC .......................................................... 600/410
See application file for complete search history.

(56) References Cited

U.S. PATENT DOCUMENTS

| | | | |
|---|---|---|---|
| 4,973,906 A | 11/1990 | Bernstein | |
| 5,652,514 A | 7/1997 | Zhang et al. | |
| 6,240,310 B1 | 5/2001 | Bundy et al. | |
| 7,412,277 B1 | 8/2008 | Saranathan et al. | |
| 8,332,010 B2 | 12/2012 | Edelman | |
| 2002/0032376 A1 | 3/2002 | Miyazaki et al. | |
| 2005/0010104 A1 | 1/2005 | Fayad et al. | |
| 2005/0065430 A1 | 3/2005 | Wiethoff et al. | |
| 2006/0184002 A1 | 8/2006 | Yarnykh et al. | |
| 2007/0265522 A1 | 11/2007 | Kassai et al. | |
| 2008/0081987 A1 | 4/2008 | Miyazaki | |
| 2010/0268062 A1 | 10/2010 | Edelman | |

FOREIGN PATENT DOCUMENTS

WO   2007124244 A1   11/2007

OTHER PUBLICATIONS

Brittain, et al., Three-Dimensional Flow-Independent Peripheral Angiography, Magnetic Resonance in Medicine, 1997, 38:343-354.
Edelman, et al., Fast Time-of-Flight MR Angiography with Improved Background Suppression, Radiology, 1991, 179:867-870.

(Continued)

*Primary Examiner* — Bo J Peng
(74) *Attorney, Agent, or Firm* — Quarles & Brady, LLP

(57) ABSTRACT

A system and method for producing an image of a vasculature of a subject using a magnetic resonance imaging (MRI) system includes applying a saturation pulse to a prescribed imaging slice to substantially suppress MR signals in the prescribed imaging slice. A quiescent inflow time period (QITP) is observed that is at least equal to half a projected duration of a cardiac cycle of the subject. After the QITP, k-space data is acquired from the prescribed imaging slice, and a subset of the data representative of a desired portion of the cardiac cycle of the subject is reconstructed into an image of the subject including at least the prescribed imaging slice.

21 Claims, 5 Drawing Sheets

(56) References Cited

OTHER PUBLICATIONS

Edelman, et al., Unenhanced Flow-Independent MR Venography by Using Signal Targeting Alternative Radiofrequency and Flow-Independent Relaxation Enhancement, Radiology, 2009, 250:236-245.

Edelman, et al., Quiescent-Interval Single-Shot Unenhanced Magnetic Resonance Angiography of Peripheral Vascular Disease: Technical Considerations and Clinical Feasibility, Magnetic Resonance in Medicine, 2010, 63 (4):951-958.

Fenchel, et al., Multislice First-Pass Myocardial Perfusion Imaging: Comparison of Saturation Recovery (SR)-TrueFISP-Two-Dimensional (2D) and SR-TurboFLASH-2D Pulse Sequences, Journal of Magnetic Resonance Imaging, 2004, 19:555-563.

Gallix, et al., Flow-Independent Magnetic Resonance Venography of the Calf, Journal of Magnetic Resonance Imaging, 2003, 17:421-426.

Katoh, et al., Free-Breathing Renal MR Angiography with Steady-State Free-Precession (SSFP) and Slab-Selective Spin Inversion: Initial Results, Kidney International, 2004, 66:1272-1278.

Lim, et al., 3D Nongadolinium-Enhanced ECG-Gated MRA of the Distal Lower Extremities: Preliminary Clinical Experience, Journal of Magnetic Resonance Imaging, 2008, 28:181-189.

Miyazaki, et al., A Novel MR Angiography Technique: Speed Acquisition Using Half-Fourier RARE, Journal of Magnetic Resonance Imaging, 1998, 8:505-507.

Miyazaki, et al., Peripheral MR Angiography: Separation of Arteries from Veins with Flow-Spoiled Gradient Pulses in Electrocardiography-Triggered Three-Dimensional Half-Fourier Fast Spin-Echo Imaging, Radiology, 2003, 227:890-896.

Nakamura, et al., Fresh Blood Imaging (FBI) of Peripheral Arteries: Comparison with 16-Detector Row CT Angiography, Proc. Intl. Soc. Mag. Reson. Med., 2006, 14:1929.

Owen, et al., Magnetic Resonance Imaging of Angiographically Occult Runoff Vessels in Peripheral Arterial Occlusive Disease, New England Journal of Medicine, 1992, 326(24):1577-1581.

Schreiber, et al., Dynamic Contrast-Enhanced Myocardial Perfusion Imaging Using Saturation-Prepared TrueFISP, Journal of Magnetic Resonance Imaging, 2002, 16:641-652.

Wright, et al., Flow-Independent Magnetic Resonance Projection Angiography, Magnetic Resonance in Medicine, 1991, 17:126-140.

Xu, et al., A Novel Non-Contrast MR Angiography Technique Using Triggered Non-Selective Refocused Space for Improved Spatial Resolution and Speed, Proc. Intl. Soc. Mag. Reson. Med., 2008, 16:730.

Yamada, et al., Visualization of Cerebrospinal Fluid Movement with Spin Labeling at MR Imaging: Preliminary Results in Normal and Pathophysiologic Conditions, Radiology, 2008; 249:644-652.

Yamashita, et al., Selective Visualization of Renal Artery Using SSFP with Time-Spatial Labeling Inversion Pulse: Non-Contrast Enhanced MRA for Patients with Renal Failure, Proc. Intl. Soc. Mag. Reson. Med., 2005, 13:1715.

Cukur, et al., Signal Compensation and Compressed Sensing for Magnetization-Prepared MR Angiography, IEEE Transactions on Medical Imaging, 2011, 30(5):1017-1027.

Fan, et al., 3D Noncontrast MR Angiography of the Distal Lower Extremities Using Flow-Sensitive Dephasing (FSD)—Prepared Balanced SSFP, Magnetic Resonance in Medicine, 2009, 62:1523-1532.

Francois, et al., Renal Arteries: Isotropic, High-Spatial-Resolution, Unenhanced MR Angiography with Three-Dimensional Radial Phase Contrast, Radiology, 2011, 258(1):254-260.

Hodnett, et al., Evaluation of Peripheral Arterial Disease with Nonenhanced Quiescent-Interval Single-Shot MR Angiography, Radiology, 2011, 260(1):282-293.

Lustig, et al., Sparse MRI: The Application of Compressed Sensing for Rapid MR Imaging, Magnetic Resonance in Medicine, 2007,58:1182-1195.

Miyazaki, et al., Nonehanced MR Angiography, Radiology, 2008, 248(1):20-43.

Scheffler, et al., Reduced Circular Field-of-View Imaging, Magnetic Resonance in Medicine, 1998, 40:474-480.

Wheaton, et al., Non-Contrast Enhanced MR Angiography: Physical Principles, Journal of Magnetic Resonance Imaging, 2012, 36:286-304.

SYSTEM AND METHOD FOR UNGATED NON-CONTRAST ENHANCED MAGNETIC RESONANCE ANGIOGRAPHY

STATEMENT REGARDING FEDERALLY SPONSORED RESEARCH

This invention was made with government support under HL096916 awarded by the National Institutes of Health. The government has certain rights in the invention.

BACKGROUND OF THE INVENTION

The field of the invention is systems and methods for magnetic resonance imaging ("MRI"). More particularly, the invention relates to systems and methods for non-contrast enhanced magnetic resonance angiography ("MRA").

When a substance such as human tissue is subjected to a uniform magnetic field (polarizing field $B_0$), the individual magnetic moments of the nuclear spins in the tissue attempt to align with this polarizing field, but precess about it in random order at their characteristic Larmor frequency. Usually the nuclear spins are comprised of hydrogen atoms, but other NMR active nuclei are occasionally used. A net magnetic moment $M_z$ is produced in the direction of the polarizing field, but the randomly oriented magnetic components in the perpendicular, or transverse, plane (x-y plane) cancel one another. If, however, the substance, or tissue, is subjected to a magnetic field (excitation field $B_1$; also referred to as the radiofrequency (RF) field) which is in the x-y plane and which is near the Larmor frequency, the net aligned moment, $M_z$, may be rotated, or "tipped" into the x-y plane to produce a net transverse magnetic moment $M_t$, which is rotating, or spinning, in the x-y plane at the Larmor frequency. The practical value of this phenomenon resides in the signal which is emitted by the excited spins after the excitation field $B_1$ is terminated. There are a wide variety of measurement sequences in which this nuclear magnetic resonance ("NMR") phenomenon is exploited.

When utilizing these signals to produce images, magnetic field gradients ($G_x$, $G_y$, and $G_z$) are employed. Typically, the region to be imaged experiences a sequence of measurement cycles in which these gradients vary according to the particular localization method being used. The emitted MR signals are detected using a receiver coil. The MRI signals are then digitized and processed to reconstruct the image using one of many well-known reconstruction techniques.

Magnetic resonance angiography (MRA) and, related imaging techniques, such as perfusion imaging, use the NMR phenomenon to produce images of the human vasculature or physiological performance related to the human vasculature. There are three main categories of techniques for achieving the desired contrast for the purpose of MR angiography. The first general category is typically referred to as contrast enhanced (CE) MRA. The second general category is phase contrast (PC) MRA. The third general category is time-of-flight (TOF) or tagging-based MRA.

Contrast-enhanced MRA techniques require venous cannulation and the use of exogenous contrast material. Such agents are costly and expose the patient to added safety risks, namely, nephrogenic systemic fibrosis. Non-enhanced techniques for MRA are helpful for the evaluation of suspected vascular disease in patients with impaired renal function, since they avoid the risk of nephrogenic systemic fibrosis.

Examples of newer non-enhanced techniques include quiescent-inflow single-shot (QISS) MRA, fresh blood imaging, and flow-sensitive dephasing, such as described in co-pending U.S. application Ser. No. 12/574,856, which is incorporated herein by reference in its entirety. QISS MRA has been shown to be a fast, accurate method for non-contrast MRA. The primary drawbacks are the need to synchronize the data acquisition to the electrocardiogram (ECG) and artifacts when severe arrhythmias are present.

In fact, most nonenhanced MRA techniques utilize cardiac gating. Notably, standard time-of-flight MRA does not utilize cardiac gating, but is, generally and unfortunately, not clinically useful for imaging outside of the head and neck. The need to apply ECG leads to the patient's chest is inconvenient and increases setup time for the MR examination. Moreover, ECG gating often fails when imaging is performed at high field strengths, such as 3 Tesla fields, due to interference from the magnetohydrodynamic effect. Moreover, some patients have a low QRS voltage or have irregular heart rhythms, which make detection of the ECG signal unreliable. Magnetic or RF interference from the scan process itself can also cause ECG gating to fail. In rare instances, the use of ECG leads has caused skin burns.

Thus, there remains a need to provide a method for non-contrast enhanced magnetic resonance angiography that is insensitive to patient motion; consistently and accurately portrays vessel anatomy, even in patients with severe vascular disease; and is less time consuming than existing methods.

SUMMARY OF THE INVENTION

The present invention overcomes the aforementioned drawbacks by providing an approach for non-contrast MRA that does not require the use of ECG gating and is insensitive to arrhythmias. Specifically, the present invention provides a non-contrast imaging technique that utilizes a quiescent inflow time period (QITP) that is greater than or equal to half and, in many cases at least an entire duration of the cardiac cycle. Doing so allows complete refreshment of saturated in-plane spins with unsaturated out-of-slice spins, even though no cardiac gating is applied. A segmented acquisition is used in which the time delay (TR) between the acquisition of sequential segments of data for a given slice is greater than the half the duration of the cardiac cycle. As a consequence, there is a substantial refreshment of in-slice spins even though the data acquisition is not synchronized to the cardiac cycle.

In accordance with one aspect of the invention, a method for producing an image of a vasculature of a subject using a magnetic resonance imaging (MRI) system includes performing a pulse sequence that directs the MRI system to apply a radio frequency (RF) saturation pulse to a prescribed imaging slice to substantially suppress MR signals in the prescribed imaging slice. The pulse sequence also directs the MRI system to apply an RF saturation pulse to a prescribed volume that is outside of the prescribed imaging slice to substantially suppress MR signals indicative of venous blood that flows into the prescribed imaging slice, observe a quiescent inflow time period (QITP) at least equal to a projected duration of a cardiac cycle of the subject, apply an RF excitation pulse to the prescribed imaging slice, and acquire k-space data from the prescribed imaging slice following the application of the RF excitation pulse as a plurality of segments in which a time delay (TR) between sequential segments in the plurality of segments for the prescribed slice is at least equal to of a projected duration of the cardiac cycle of the subject determining a subset of the acquired k-space data which is representative of a desired portion of the cardiac cycle of the subject and reconstructing, from the subset of acquired k-space data which is representative of the desired portion of the cardiac cycle, an image of the subject including at least the prescribed imaging slice over the desired portion of the cardiac cycle.

In accordance with another aspect of the invention, a magnetic resonance imaging (MRI) system is disclosed that includes a magnet system configured to generate a polarizing magnetic field about at least a region of interest (ROI) in a subject arranged in the MRI system, a plurality of gradient coils configured to apply a gradient field to the polarizing magnetic field, and a radio frequency (RF) system configured to apply an excitation field to the subject and acquire MR image data from a ROI. The MRI system also includes a computer system programmed to control the RF system and gradient coils to apply a saturation pulse to a prescribed imaging slice to substantially suppress MR signals in the prescribed imaging slice and control the RF system and gradient coils to apply an RF saturation pulse to a prescribed volume that is outside of the prescribed imaging slice to substantially suppress MR signals indicative of venous blood that flows into the prescribed imaging slice. The computer system is further configured to observe a quiescent inflow time period (QITP) at least equal to half a projected duration of a cardiac cycle of the subject, control the RF system and gradient coils to apply an RF excitation pulse to the prescribed imaging slice, and acquire k-space data from the prescribed imaging slice as a plurality of segments. The computer system is configured to reconstruct, from the acquired k-space data, an image of the subject including at least the prescribed imaging slice.

In accordance with yet another aspect of the invention, a method for producing an image of a vasculature of a subject using a magnetic resonance imaging (MRI) system is disclosed that includes performing a pulse sequence that directs the MRI system to apply a radio frequency (RF) saturation pulse to a prescribed imaging slice to substantially suppress MR signals in the prescribed imaging slice. The pulse sequence may also direct the MRI system to apply an RF saturation pulse to a prescribed volume that is outside of the prescribed imaging slice to substantially suppress MR signals indicative of venous blood that flows into the prescribed imaging slice and observe a quiescent inflow time period (QITP) selected to allow a refreshment of saturated in-plane spins in the prescribed imaging slice with unsaturated out-of-slice spins without timing the QITP with respect to a cardiac gating signal.

In accordance with still another aspect of the invention, a method for producing an image of a vasculature of a subject using a magnetic resonance imaging (MRI) system is disclosed that includes applying a saturation pulse to a prescribed imaging slice to substantially suppress MR signals in the prescribed imaging slice and applying an RF saturation pulse to a prescribed volume that is outside of the prescribed imaging slice to substantially suppress MR signals indicative of venous blood that flows into the prescribed imaging slice. A quiescent inflow time period (QITP) is observed that is at least equal to half a projected duration of a cardiac cycle of the subject. After the QITP, k-space data is acquired from the prescribed imaging slice as a plurality of segments. A subset of the acquired k-space data which is representative of slow diastolic flow is reconstructed into an image of the subject including at least the prescribed imaging slice.

The foregoing and other aspects of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
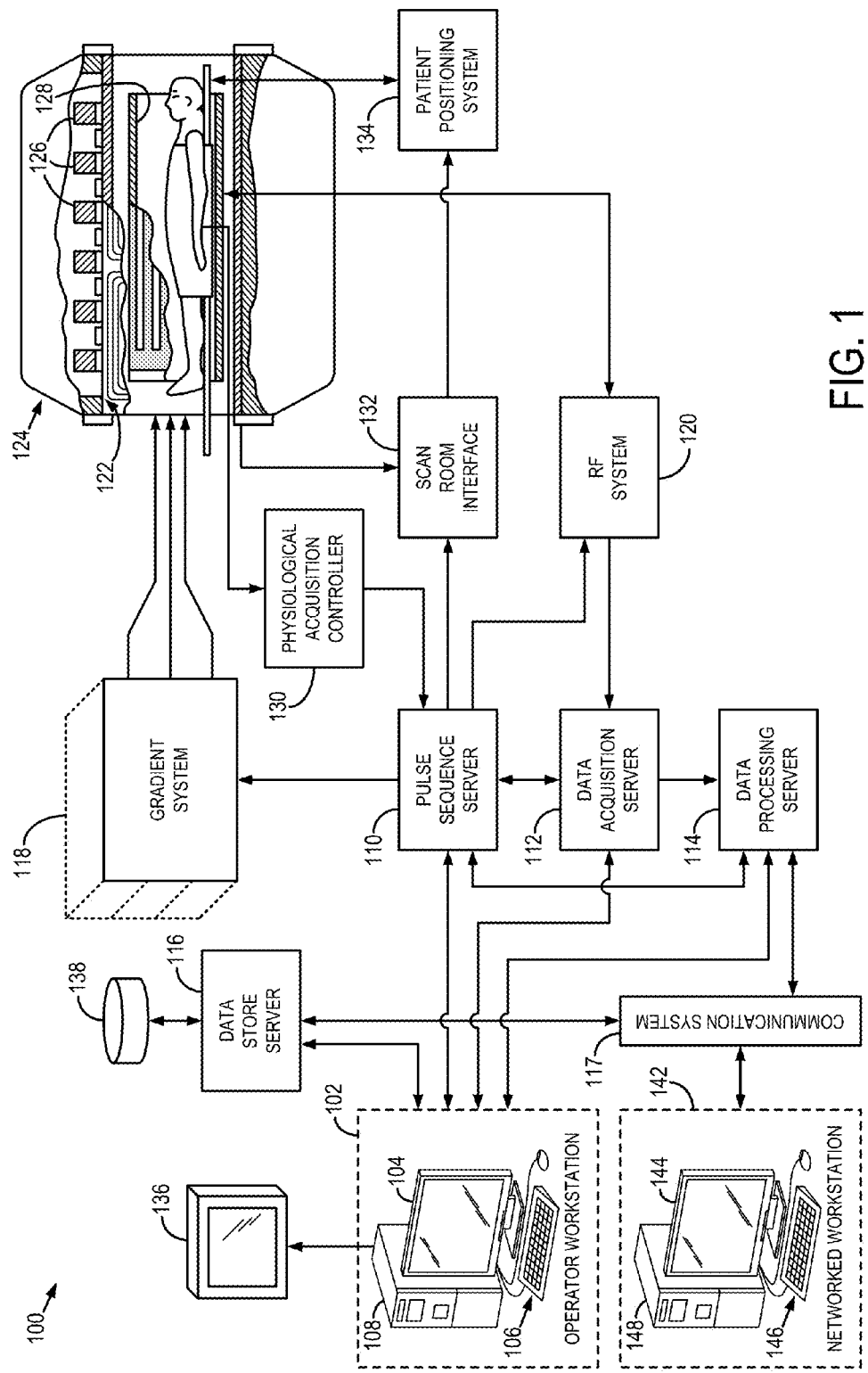
FIG. 1 is a schematic diagram of a magnetic resonance imaging system configured for use with the present invention.

Referring particularly now to FIG. 1, an example of a magnetic resonance imaging (MRI) system 100 is illustrated. The MRI system 100 includes an operator workstation 102, which will typically include a display 104, one or more input devices 106, such as a keyboard and mouse, and a processor 108. The processor 108 may include a commercially available programmable machine running a commercially available operating system. The operator workstation 102 provides the operator interface that enables scan prescriptions to be entered into the MRI system 100. In general, the operator workstation 102 may be coupled to four servers: a pulse sequence server 110; a data acquisition server 112; a data processing server 114; and a data store server 116. The operator workstation 102 and each server 110, 112, 114, and 116 are connected to communicate with each other. For example, the servers 110, 112, 114, and 116 may be connected via a communication system 117, which may include any suitable network connection, whether wired, wireless, or a combination of both. As an example, the communication system 117 may include both proprietary or dedicated networks, as well as open networks, such as the internet.

The pulse sequence server 110 functions in response to instructions downloaded from the operator workstation 102 to operate a gradient system 118 and a radiofrequency ("RF") system 120. Gradient waveforms necessary to perform the prescribed scan are produced and applied to the gradient system 118, which excites gradient coils in an assembly 122 to produce the magnetic field gradients $G_x$, $G_y$, and $G_z$ used for position encoding magnetic resonance signals. The gradient coil assembly 122 forms part of a magnet assembly 124 that includes a polarizing magnet 126 and a whole-body RF coil 128.

RF waveforms are applied by the RF system 120 to the RF coil 128, or a separate local coil (not shown in FIG. 1), in order to perform the prescribed magnetic resonance pulse sequence. Responsive magnetic resonance signals detected by the RF coil 128, or a separate local coil (not shown in FIG. 1), are received by the RF system 120, where they are amplified, demodulated, filtered, and digitized under direction of commands produced by the pulse sequence server 110. The RF system 120 includes an RF transmitter for producing a wide variety of RF pulses used in MRI pulse sequences. The RF transmitter is responsive to the scan prescription and direction from the pulse sequence server 110 to produce RF pulses of the desired frequency, phase, and pulse amplitude waveform. The generated RF pulses may be applied to the whole-body RF coil 128 or to one or more local coils or coil arrays (not shown in FIG. 1).

The RF system 120 also includes one or more RF receiver channels. Each RF receiver channel includes an RF preamplifier that amplifies the magnetic resonance signal received by the coil 128 to which it is connected, and a detector that detects and digitizes the I and Q quadrature components of the received magnetic resonance signal. The magnitude of the received magnetic resonance signal may, therefore, be determined at any sampled point by the square root of the sum of the squares of the I and Q components:

$$M=\sqrt{I^2+Q^2} \qquad \text{Eqn. 1;}$$

and the phase of the received magnetic resonance signal may also be determined according to the following relationship:

$$\varphi = \tan^{-1}\left(\frac{Q}{I}\right). \qquad \text{Eqn. 2}$$

The pulse sequence server 110 also optionally receives patient data from a physiological acquisition controller 130. By way of example, the physiological acquisition controller 130 may receive signals from a number of different sensors connected to the patient, such as electrocardiograph ("ECG") signals from electrodes, or respiratory signals from a respiratory bellows or other respiratory monitoring device. Such signals are typically used by the pulse sequence server 110 to synchronize, or "gate," the performance of the scan with the subject's heart beat or respiration.

The pulse sequence server 110 also connects to a scan room interface circuit 132 that receives signals from various sensors associated with the condition of the patient and the magnet system. It is also through the scan room interface circuit 132 that a patient positioning system 134 receives commands to move the patient to desired positions during the scan.

The digitized magnetic resonance signal samples produced by the RF system 120 are received by the data acquisition server 112. The data acquisition server 112 operates in response to instructions downloaded from the operator workstation 102 to receive the real-time magnetic resonance data and provide buffer storage, such that no data is lost by data overrun. In some scans, the data acquisition server 112 does little more than pass the acquired magnetic resonance data to the data processor server 114. However, in scans that require information derived from acquired magnetic resonance data to control the further performance of the scan, the data acquisition server 112 is programmed to produce such information and convey it to the pulse sequence server 110. For example, during prescans, magnetic resonance data is acquired and used to calibrate the pulse sequence performed by the pulse sequence server 110. As another example, navigator signals may be acquired and used to adjust the operating parameters of the RF system 120 or the gradient system 118, or to control the view order in which k-space is sampled. In still another example, the data acquisition server 112 may also be employed to process magnetic resonance signals used to detect the arrival of a contrast agent in a magnetic resonance angiography (MRA) scan. By way of example, the data acquisition server 112 acquires magnetic resonance data and processes it in real-time to produce information that is used to control the scan.

The data processing server 114 receives magnetic resonance data from the data acquisition server 112 and processes it in accordance with instructions downloaded from the operator workstation 102. Such processing may, for example, include one or more of the following: reconstructing two-dimensional or three-dimensional images by performing a Fourier transformation of raw k-space data; performing other image reconstruction algorithms, such as iterative or back-projection reconstruction algorithms; applying filters to raw k-space data or to reconstructed images; generating functional magnetic resonance images; calculating motion or flow images; and so on.

Images reconstructed by the data processing server 114 are conveyed back to the operator workstation 102 where they are stored. Real-time images are stored in a data base memory cache (not shown in FIG. 1), from which they may be output to operator display 112 or a display 136 that is located near the magnet assembly 124 for use by attending physicians. Batch mode images or selected real time images are stored in a host database on disc storage 138. When such images have been reconstructed and transferred to storage, the data processing server 114 notifies the data store server 116 on the operator workstation 102. The operator workstation 102 may be used by an operator to archive the images, produce films, or send the images via a network to other facilities.

The MRI system 100 may also include one or more networked workstations 142. By way of example, a networked workstation 142 may include a display 144; one or more input devices 146, such as a keyboard and mouse; and a processor 148. The networked workstation 142 may be located within the same facility as the operator workstation 102, or in a different facility, such as a different healthcare institution or clinic.

The networked workstation 142, whether within the same facility or in a different facility as the operator workstation 102, may gain remote access to the data processing server 114 or data store server 116 via the communication system 117. Accordingly, multiple networked workstations 142 may have access to the data processing server 114 and the data store server 116. In this manner, magnetic resonance data, reconstructed images, or other data may exchanged between the data processing server 114 or the data store server 116 and the networked workstations 142, such that the data or images may be remotely processed by a networked workstation 142. This data may be exchanged in any suitable format, such as in accordance with the transmission control protocol (TCP), the internet protocol (IP), or other known or suitable protocols.

Figure 2:
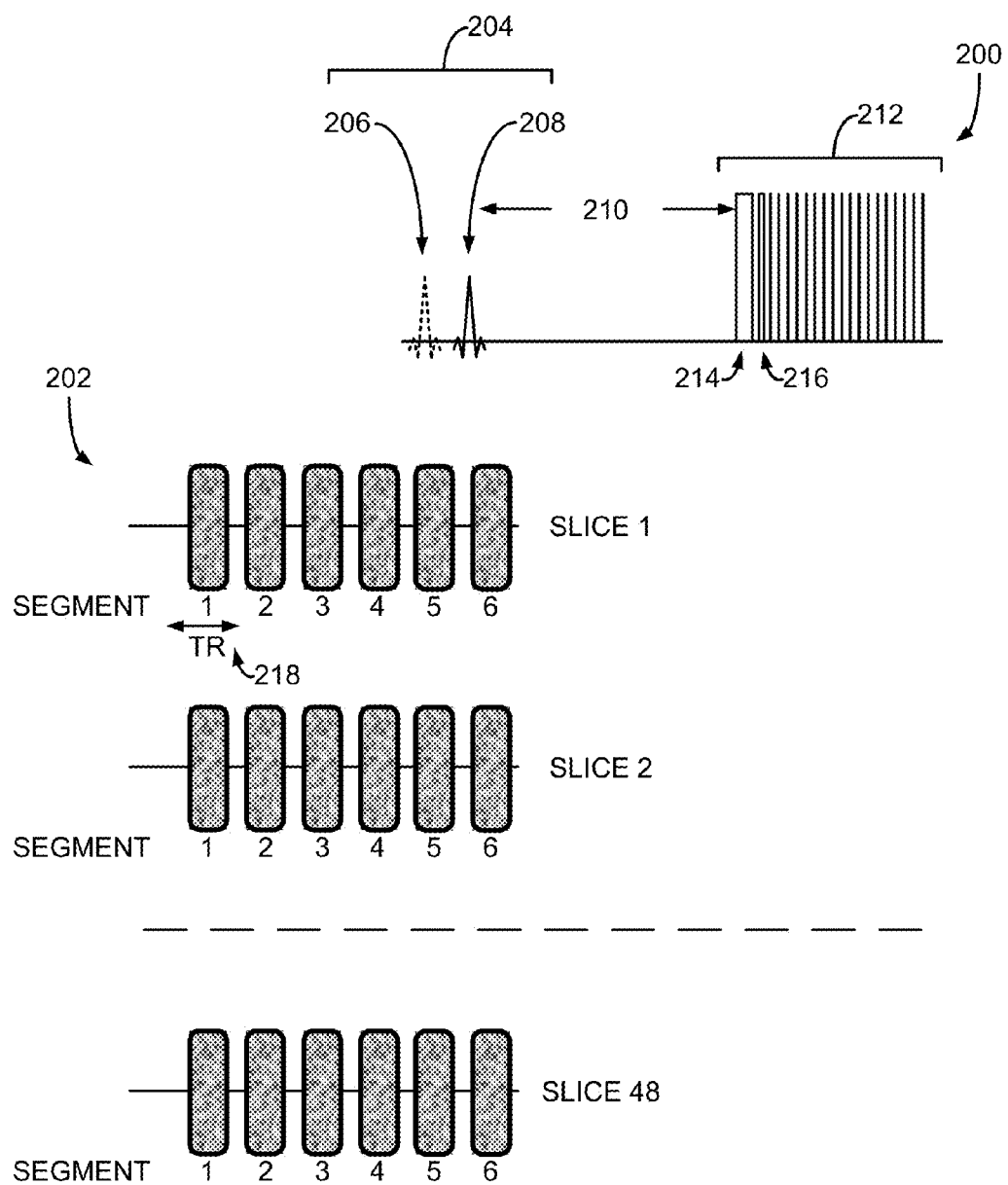
FIG. 2 is a general diagram of a pulse sequence and segment acquisition process.

The above-described MRI system 100 or other MRI system may be utilized to carry out a method for non-cardiac-gated, non-contrast-enhanced MRI in accordance with the present invention. More particularly, a method for non-cardiac-gated non-contrast-enhanced magnetic resonance angiography ("MRA") may be performed using the above-described MRI system 100. Referring to FIG. 2, a pulse sequence 200 to be performed by the above-described MRI and associated slice/segments 202 resulting therefrom are illustrated. As will be described, FIG. 2 illustrates a pulse sequence diagram in accordance with the present invention using in-plane inversion, tracking venous saturation, 6 segments, and 48 slices.

The pulse sequence 200 includes a magnetization preparation module 204 that may include at least one inversion pulse 206 or a saturation pulse 208. The preparation module 204 is applied to spins in an imaging slice and, optionally, to inflowing venous spins outside of the imaging slice. Thus, the inversion pulse 206 is directed to the imaging slice, as will be further described, and the saturation pulse 208 is targets venous spins. A quiescent inflow time period ("QITP") 210, during which no RF pulses are applied, is performed by the system, followed by a data acquisition module 212. As will be described, the QITP is preferably selected to be greater than or equal to a projected duration of the subject's cardiac cycle, which may be, for example, an average (subject or baseline average) or other estimate or means for projecting the duration of the subject's cardiac cycle. That is, notably and preferably, the QITP 210 is selected to be greater than or equal to the duration of the subject's cardiac cycle, which ensures that the saturated in-place spins are completely replaced with unsaturated out-of-slice spins, even though no cardiac gating is applied. However, as will be described below, the present invention provides techniques to reduce the QITP to approximately half or more than the projected duration of the cardiac cycle even though no cardiac gating is applied, while still yielding clinically-useful images.

The data acquisition module 212 may include, for example, further preparations, such as a fat saturation pulse 214 and/or an alpha/2 preparation 216. As will be further described, the alpha/2 magnetization preparation 216 may precede each segment. The data acquisition module 212 may also include, for example, a pulse sequence, such as balanced steady-state free precession ("bSSFP"). As a further example, the bSSFP pulse sequence may elicit a segmented, two-dimensional bSSFP data acquisition. Moreover, the data acquisition module 212 is configured to acquire a stack of contiguous or overlapping slices 202 such that one segment of data for an imaging slice is acquired within one repetition time ("TR") 218 and the time interval between the acquisition of successive segments for any imaging slice is greater than or equal to the TR 218. As a consequence, there is a relatively random distribution of flow-induced phase shifts throughout k-space, thereby minimizing signal loss and ghost artifacts in the resulting images, even though the data acquisition is not synchronized to the cardiac cycle.

Figure 3:
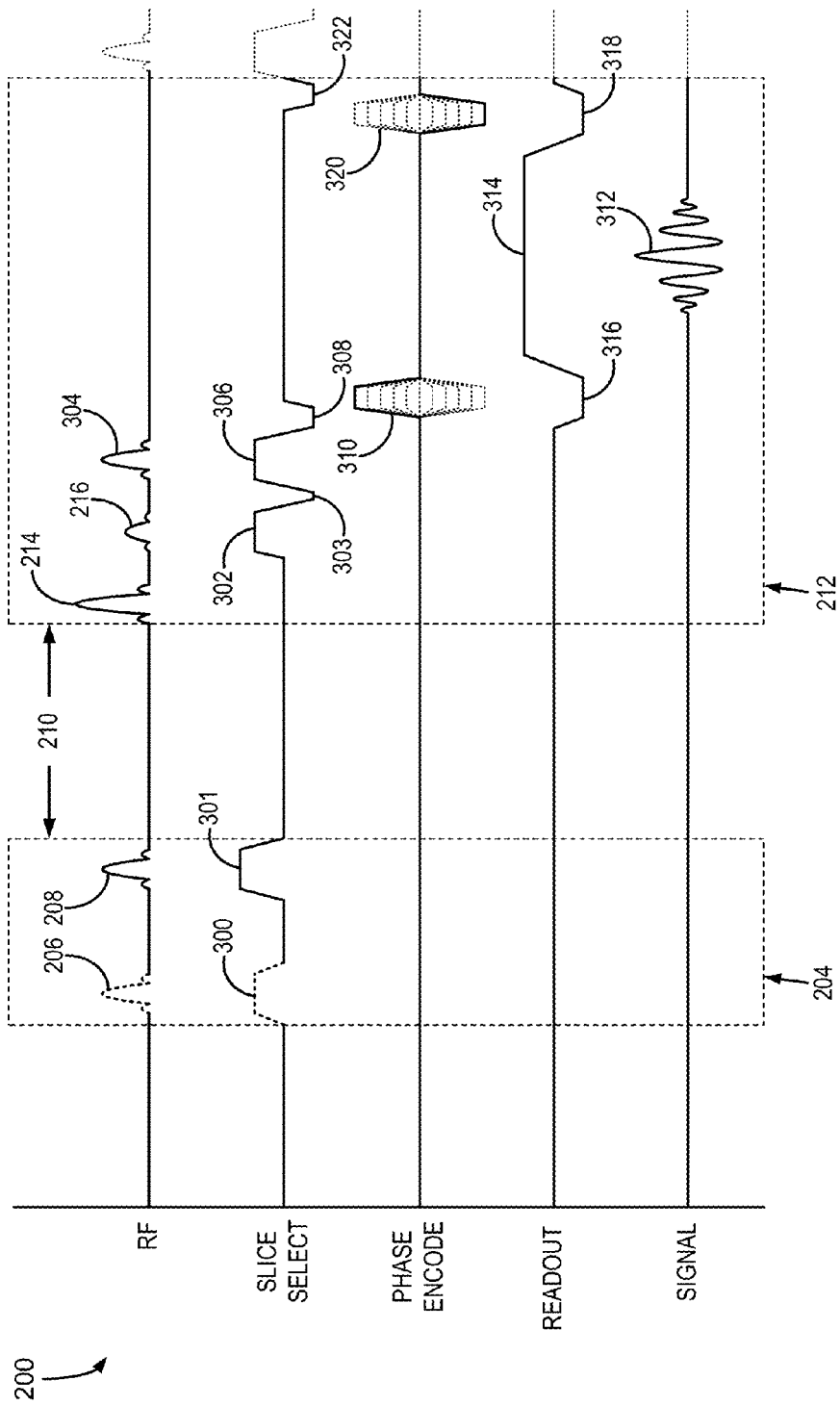
FIG. 3 is a detailed pulse sequence diagram of one implementation if a pulse sequence in accordance with the present invention.

Referring now particularly to FIG. 3, the above-described pulse sequence is pictorially shown in further detail. Notably, the pulse sequence 200 is not cardiac gated, such that the acquisition of k-space data is not precisely timed with respect to the flow of arterial blood. As described above, the pulse sequence 200 generally includes the magnetization preparation module 204, a QITP 210 in which no radio frequency ("RF") pulses are applied, and a data acquisition module 212.

The magnetization preparation module 204 typically uses at least one inversion 206 and/or saturation 208 RF pulse. RF saturation pulses 208 differ from inversion recovery pulses 206, in that using an RF saturation pulse 208 resets the longitudinal magnetization to zero prior to the beginning of the QITP 210. This may not be the case when using inversion recovery pulses 206 because inadequate inversion of the spins may leave residual longitudinal magnetization at the beginning of the QITP 210. This residual longitudinal magnetization can confound the subsequently detected MR signals. RF saturation pulses 208 also have the added benefit that, because the longitudinal magnetization is reset to zero, the use of slice-selection ensures that the tissue signal remains substantially uniform across different slices despite variations in the subject's cardiac cycle that may result from cardiac arrhythmias.

The inversion/saturation pulse 206, 208 is generally applied in-plane, as indicated by associated slice-select gradients 300, 301, to suppress the signal intensity of background tissue, including static venous spins. Optionally, a saturation or inversion RF pulse can be applied to out-of-plane venous spins to further suppress their contribution to the signal that will be acquired during the subsequent data acquisitions. Saturation or inversion of the out-of-plane venous spins reduces their longitudinal magnetization, thereby suppressing venous signal as these spins flow into the imaging slice over the QITP 210. By combining the effect of the in-plane magnetization preparation and out-of-plane saturation the present invention is able to ensure adequate suppression of venous signal irrespective of flow rate. Accordingly, as noted above, the present invention does not require cardiac gating or synchronization to the cardiac cycle.

After the QITP 210 has passed, the pulse sequence 200 proceeds with the data acquisition module 212, which is accomplished, for example, with a single shot balanced steady-state free procession (SSFP) gradient echo pulse sequence. First, a spectrally selective fat saturation RF pulse 214 is applied to further suppress unwanted MR signals originating from fat tissue. This is subsequently followed by a slice-selective α/2 magnetization RF pulse 216 that is played out in the presence of a slice-selective gradient 302, where α is a user selected flip angle. The slice-selective gradient 300 includes a rephasing lobe 303 that acts to mitigate unwanted phase accruals that occur during the application of the slice-selective gradient 302. This portion of the pulse sequence 200 includes a slice-selective RF excitation pulse 304 that is played out in the presence of a slice-selective gradient pulse 306 to produce transverse magnetization in a prescribed slice. The slice-selective gradient pulse 306 includes a rephasing lobe 308 that acts to mitigate unwanted phase accruals that occur during the application of the slice-selective gradient 306. After excitation of the spins in the slice, a phase encoding gradient pulse 310 is applied to position encode the MR signal 312 along one direction in the slice. A readout gradient pulse 314 is also applied after a dephasing gradient lobe 316 to position encode the MR signal 312 along a second, orthogonal direction in the slice. Like the slice-selective gradient 306, the readout gradient 314 also includes a rephasing lobe 318 that acts to mitigate unwanted phase accruals.

To maintain the steady state condition, the integrals along the three gradients each sum to zero during the repetition time ("TR") period. To accomplish this, a rewinder gradient lobe 320 that is equal in amplitude, but opposite in polarity of the phase encoding gradient 310, is played out along the phase encoding gradient axis. Likewise, a dephasing lobe 322 is added to the slice select gradient axis, such that the dephasing lobe 322 precedes the repetition of the slice-selective gradient 306 in the next TR period. As is well known in the art, the reading out of MR signals following the single shot of the RF excitation pulse 304 is repeated and the amplitude of the phase encoding gradient 310 and its equal, but opposite rewinder 320 are stepped through a set of values to sample 2D k-space in a prescribed manner. It should be appreciated by those skilled in the art that any number of data acquisition schemes can be employed to acquire k-space data instead of balanced SSFP. For example, spoiled gradient echo, spiral acquisition, or echo planar imaging ("EPI") pulse sequences can alternatively be utilized.

Of course, multiple variations on the above-described pulse sequence are contemplated. For example, the magnetization preparation module may include two RF pulses, namely, an inversion pulse 206 narrowly applied to the slice based on gradient 300 and a saturation pulse 208 broadly applied based on gradient 301 to inflowing venous spins. The order of these pulses 206, 208 can be reversed without substantially altering the image appearance.

As another example, a single large inversion region can be applied simultaneously to both the inflowing venous spins and imaging slice prior to the QITP 210. A drawback of using a single inversion region is that the edge profile of a large inversion slab is less sharp compared with that of a narrow slice, which may cause uneven suppression of background tissues and inadvertent suppression of inflowing arterial spins.

Furthermore, alternative pulse sequences for data readout are likewise available. Examples include a spoiled gradient-echo acquisition instead of a bSSFP gradient-echo acquisition, although this would be anticipated to result in a reduced signal-to-noise ratio ("SNR"). Notably, a variety of k-space trajectories can be used, including Cartesian, radial, echo planar, or spiral, as well as a variety of methods to shorten the data acquisition period.

A variety of methods can be employed to achieve the above-described fat suppression, including chemical shift-selective RF pulses, water-selective excitation, Dixon techniques, and various other approaches. Although an axial orientation is often preferred for many clinical settings, other slice orientations can be used as well. Background suppression may be improved by subtracting, what will be described as an "UNQISS" MRA acquisition, using a superiorly positioned saturation module from one using an inferiorly positioned saturation module. However, this process increases scan time and makes the acquisition more sensitive to motion.

Notably, though the QITP 210 is described above as being generally free of RF pulses, it is possible to use the time interval during the QITP 210 to apply additional RF pulses and/or acquire additional image data which could be used for demonstration of anatomy, flow direction, image subtraction, to alter tissue contrast, and so forth. It should be noted, however, that any RF pulses applied during the QITP 210 may cause saturation of inflowing arterial spins and reduce arterial conspicuity and, thus, are to be carefully selected and crafted.

Figure 4:
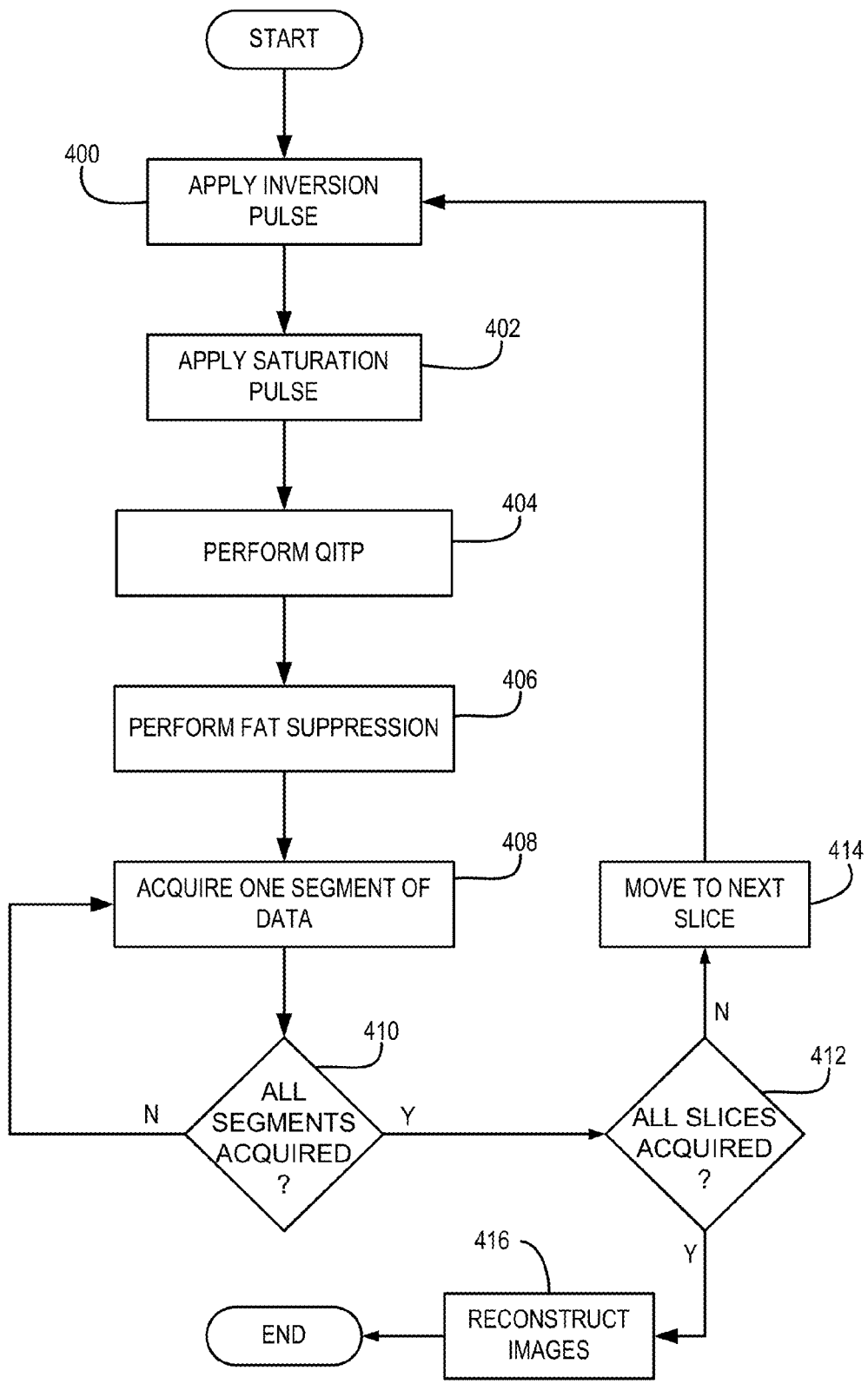
FIG. 4 is a flow chart setting forth the steps of a method in accordance with the present invention.

Referring to FIG. 4, an imaging process employing the above-described pulse sequence and using an MRI system, such as described above, begins at process block 400 with the application of a slice-selective inversion RF pulse that is applied to the slice in order to suppress the signal intensity of fluid, edema, fat, muscle, stationary venous spins and other background tissues. At process block 402, a tracking saturation RF pulse may be applied. In one example, the saturation RF pulse may be a 100 mm-thick and applied caudally, such that the top of the saturated region is contiguous with the imaging slice. The general purpose of the saturation pulse applied at process block 402 is to suppress the signal from moving venous spins.

At process block 404, a quiescent inflow time period (QITP) is performed. In one example, the QITP may have a duration selected to roughly span the projected duration of, for example, an average cardiac cycle of the subject being imaged. Alternatively the projected duration may be that of a baseline study or other set of criteria upon which to project the duration of the subject's cardiac cycle without direct measurement or systems for gating. For some subjects, the QITP may have a duration, for example of 900 ms. By design, the QITP allows for unsaturated arterial spins to flow into the imaging slice and replace the saturated spins. Since no or few RF pulses are applied during the QITP, there is no (or at least controlled) saturation of the inflowing spins to create a desired arterial conspicuity. Moreover, the QITP affords the opportunity for out-of-slice saturated venous spins to flow into and through the imaging slice, ensuring that venous signal is suppressed.

At process block 406, a fat suppression technique may be applied. The fat suppression technique may be a chemical shift-selective fat saturation RF pulse or other fat suppression technique. Next, at process block 408, one segment of data is acquired using, for example, a 2D balanced steady-state free precession (bSSFP) pulse sequence. The duration of each segment of the bSSFP acquisition must be kept short, typically less than two hundred milliseconds, in order to maintain adequate suppression of signal from background tissues as well as to minimize flow-related phase shifts, motion sensitivity, and RF power deposition.

After the data has been acquired, a check is made at decision block 410 to determine if all data has been acquired for each segment, if not, the process is repeated for the next segment. Once all data for a given segment is collected, a check is made at decision block 412 to determine if data from all desired slices has been acquired. If not, the process moves, at process block 414, to the next slice. This process is repeated until data for all segments and all the slices have been acquired. Once all of the data is acquired, at process block 416, the data may be reconstructed into the desired images. The images can be processed using a maximum intensity projection or other 3D processing methods.

By way of example only, one acquisition may employ 2-8 segments and 32-128 slices. Notably, to acquire data across the multiple slices, it may be desirable to move the subject to various imaging stations. By way of example, 64 slightly overlapping 3 mm-thick slices may be acquired for one station, followed by a shift in table position, and acquisition of a contiguous group of slices. This process is designed to ensure that the magnetic field can be shimmed to sufficient uniformity over each slice group. If too many slices are acquired in a single group such that the outer slices are far outside the isocenter of the magnet, then artifacts may occur due to imperfect shimming. Depending on patient height, approximately eight groups of 64 slices may be used to span the peripheral arteries from the level of the distal aorta to the pedal arteries. For regions such as the abdomen where breath-holding is required, a reduced number of slices is acquired per station.

Notably, in many clinical applications, it is desirable that the slice acquisition order be opposite to the direction of arterial blood flow. A technique variation involves applying a saturation pulse to inflowing venous spins without applying a magnetization preparation to the slice. This will suppress venous signal but allow visualization of the arteries. However, in this scenario one will also visualize fluids and tissue edema, which may degrade the image quality on a maximum intensity projection.

Several other technique variations are contemplated. For instance, within each TR interval, a single venous saturation could be applied, followed by in-plane inversion of one or more additional adjacent slices in rapid succession, followed by QITP, followed by additional data readouts for the one or more slices in rapid succession. This approach will reduce scan time by a factor of at least two compared with a single slice readout. Scan time can be further reduced using parallel imaging or partial Fourier techniques.

The proposed invention has the advantages of speed, robustness, and simplicity. For instance, the entire length of the peripheral arteries can be imaged in less than 30 minutes with high arterial conspicuity and marked suppression of venous signal. No ECG gating is needed, greatly simplifying patient setup and convenience. Moreover, with appropriate choice of sequence parameters, one does not even need to acquire a scout image for slice positioning.

Three-dimensional acquisitions, such as fresh blood imaging, are generally too time-consuming to permit data acquisition within a single breath-holding period. In contrast, with the above described "UNQISS" MRA techniques it is straightforward to acquire a group of slices within a single breath-hold. The capability for breath-holding enables artifacts from vessel misregistration to be eliminated in regions like the abdomen and pelvis.

Therefore, the present invention provides a method that controls the signals from veins, which is challenging since venous blood flows only a short distance or not at all during the short scan time, and provides accurate depiction of arterial anatomy over a wide range of flow velocities, ranging from a few cm/sec to more than 100 cm/sec, with sufficient arterial conspicuity to allow creation of a projection angiogram. By controlling venous signals, the present method overcomes the drawbacks of prior systems and method that fail to provide similar control and, thus, venous signal using those traditional methods tends to overlap the arterial signals on projection images making it difficult or impossible to use the MRA to diagnose arterial disease.

The present invention provides a combination of an in-slice magnetization preparation (with or without venous saturation), quiescent interval to permit inflow of unsaturated arterial spins, segmented 2D bSSFP data acquisition, and countercurrent slice acquisition that is clinically advantageous and particularly advantageous when considered with respect to traditional techniques that have focused on similar clinical applications.

Figure 5:
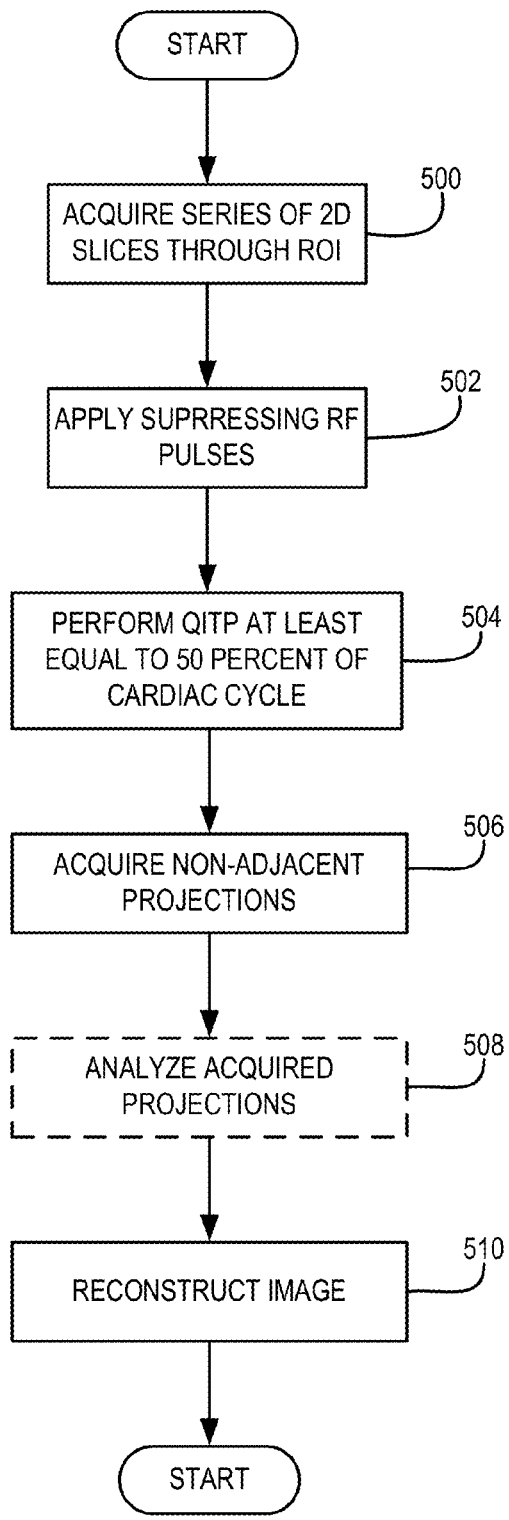
FIG. 5 is a flow chart setting forth the steps of a method in accordance with the present invention.

Referring to FIG. 5, another flow chart is provided that sets forth the steps of another method for nonenhanced MRA without cardiac gating. The process begins at process block 500 the acquisition of a series of two-dimensional (2D) slices through a region of interest (ROI). At process block 502, for each 2D slice, one or more initial in-plane RF pulses are applied so as to suppress the signal intensity of blood vessels and background tissue.

At process block 504, following the RF pulse(s), a delay time (the quiescent interval, QI or QITP) is applied to allow for inflow of unsaturated spins into the slice. The QI should be at least 50 percent of the projected, expected, or estimated duration of the cardiac cycle of the subject. As described above, the QITP may be advantageously at least equal to the projected duration of the entire cardiac cycle so as to allow for complete refreshment of spins prior to data acquisition irrespective of the phase of the cardiac cycle.

At process block 506, data is sequentially acquired using a series of non-adjacent projections. In accordance with the present method, these projections may, advantageously, each sample the center of k-space. The non-adjacent pattern, such as achieved, for example, by using a golden angle or pseudorandom radial k-space trajectory, reduces the likelihood that sequentially acquired projections will represent the same phase of the cardiac cycle, thereby further controlling flow artifacts.

Optionally, at process block 508, the acquired projections may be analyzed, for example, by reconstructing subsets of projections and identifying projections producing anomalous vascular signal, so that projections representing periods of rapid or accelerating flow (which cause flow artifacts) may be selectively discarded prior to reconstruction of the MRA images. At process block 510, the projections are reconstructed into MRA images. For example, as part of the reconstruction process, the images may be re-projected (e.g. using a maximum intensity projection algorithm) so as to display an MRA image.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for producing an image of a vasculature of a subject using a magnetic resonance imaging (MRI) system, the steps comprising:
a) performing a pulse sequence that directs the MRI system to:
   i) apply a radio frequency (RF) saturation pulse to a prescribed imaging slice to suppress MR signals in the prescribed imaging slice;
   ii) observe a quiescent inflow time period (QITP) at least equal to a projected duration of a cardiac cycle of the subject;
   iii) apply an RF excitation pulse to the prescribed imaging slice;
   iv) acquire k-space data from the prescribed imaging slice following the application of the RF excitation pulse as a plurality of segments in which a time delay (TR) between sequential segments in the plurality of segments for the prescribed slice is at least equal to of a projected duration of the cardiac cycle of the subject; and
b) determining a subset of the acquired k-space data which is representative of a desired portion of the cardiac cycle of the subject;
c) reconstructing, from the subset of acquired k-space data which is representative of the desired portion of the cardiac cycle, an image of the subject including at least the prescribed imaging slice over the desired portion of the cardiac cycle; and
wherein the TR is selected to allow a random distribution of flow-induced phase shifts to accumulate throughout k-space to control signal loss and artifact-inducing components in the k-space data without synchronization to the cardiac cycle.

2. The method of claim 1 wherein step a) is repeated for a plurality of prescribed imaging slices spanning a region of interest (ROI) including the vasculature.

3. The method of claim 1 wherein steps a)ii), a)iii), and a)iv) are configured to suppress MR signals within the prescribed imaging slice from venous blood irrespective of flow rate of the venous blood.

4. The method of claim 1 wherein step a) further comprises apply an RF saturation pulse to a prescribed volume that is outside of the prescribed imaging slice to suppress MR signals indicative of venous blood that flows into the prescribed imaging slice and wherein QITP is selected to allow a refreshment of saturated in-plane spins in the prescribed imaging slice to be replaced with unsaturated out-of-slice spins without timing the QITP with respect to a cardiac gating signal.

5. The method of claim 1 wherein the vasculature is free of contrast agents.

6. The method of claim 1 wherein step a) is repeated a plurality of times and, for occurrence of step a)iv):
for each TR associated with each occurrence of step a)v), apply:
a venous saturation pulse;
an in-plane inversion of at least one adjacent slice to the prescribed imaging slice;
a QITP; and
acquire k-space data from the at least one adjacent slice.

7. A magnetic resonance imaging (MRI) system comprising:
a magnet system configured to generate a polarizing magnetic field about at least a region of interest (ROI) in a subject arranged in the MRI system;
a plurality of gradient coils configured to apply a gradient field to the polarizing magnetic field;
a radio frequency (RF) system configured to apply an excitation field to the subject and acquire MR image data from a ROI;
a computer system programmed to:
a) control the RF system and gradient coils to apply a saturation pulse to a prescribed imaging slice to suppress MR signals in the prescribed imaging slice;
b) control the RF system and gradient coils to apply an RF saturation pulse to a prescribed volume that is outside of the prescribed imaging slice to suppress MR signals indicative of venous blood that flows into the prescribed imaging slice;

c) observe a quiescent inflow time period (QITP) at least equal to half a projected duration of a cardiac cycle of the subject;

d) control the RF system and gradient coils to apply an RF excitation pulse to the prescribed imaging slice;

e) acquire k-space data from the prescribed imaging slice as a plurality of segments in which a time delay (TR) between sequential segments in the plurality of segments for the prescribed imaging slice is selected to allow a random distribution of flow-induced phase shifts to accumulate throughout k-space to control signal loss and artifact-inducing components in the k-space data without synchronization to the cardiac cycle; and f) reconstruct, from the acquired k-space data, an image of the subject including at least the prescribed imaging slice.

8. The MRI system of claim 7 wherein the computer system is configured to select the QITP to allow a refreshment of saturated in-plane spins in the prescribed imaging slice to be replaced with unsaturated out-of-slice spins without timing the QITP with respect to a cardiac gating signal.

9. The MRI system of claim 7 wherein the TR is at least equal to half a projected duration of the cardiac cycle of the subject.

10. The MRI system of claim 9 wherein the computer is further configure to repeated a) through e) a plurality of times and, for occurrence of e):

for each TR associated with each occurrence of step e), apply:
a venous saturation pulse;
an in-plane inversion of at least one adjacent slice to the prescribed imaging slice;
a QITP; and
acquire k-space data from the at least one adjacent slice.

11. The MRI system of claim 7 wherein the computer system is further configured to control the RF system acquire a coil sensitivity map.

12. The MRI system of claim 11 wherein the computer system is configured to perform e) using parallel receive techniques.

13. A method for producing an image of a vasculature of a subject using a magnetic resonance imaging (MRI) system, the steps comprising:

a) performing a pulse sequence that directs the MRI system to:
i) apply a radio frequency (RF) saturation pulse to a prescribed imaging slice to suppress MR signals in the prescribed imaging slice;
ii) apply an RF saturation pulse to a prescribed volume that is outside of the prescribed imaging slice to suppress MR signals indicative of venous blood that flows into the prescribed imaging slice;
iii) observe a quiescent inflow time period (QITP) selected to allow a refreshment of saturated in-plane spins in the prescribed imaging slice with unsaturated out-of-slice spins without timing the QITP with respect to a cardiac gating signal;
iv) apply an RF excitation pulse to the prescribed imaging slice;
v) acquire k-space data from the prescribed imaging slice following the application of the RF excitation pulse as a plurality of segments in which a time delay (TR) between sequential segments in the plurality of segments for the prescribed slice is selected to allow a random distribution of flow-induced phase shifts to accumulate throughout k-space to control signal loss and artifact-inducing components in the k-space data without synchronization to the cardiac cycle;

c) reconstructing, from the acquired k-space data, an image of the subject including at least the prescribed imaging slice.

14. The method of claim 13 wherein step a) is repeated for a plurality of prescribed imaging slices spanning a region of interest (ROI) including the vasculature.

15. The method of claim 13 wherein steps a)ii), a)iii), and a)iv) are configured to suppress MR signals within the prescribed imaging slice from venous blood irrespective of flow rate of the venous blood.

16. The method of claim 13 wherein the QITP is selected to allow a refreshment of saturated in-plane spins in the prescribed imaging slice to be replaced with unsaturated out-of-slice spins without timing the QITP with respect to a cardiac gating signal.

17. A method for producing an image of a vasculature of a subject using a magnetic resonance imaging (MRI) system, the steps comprising:

a) controlling an RF system and gradient coils of the MRI system to apply a saturation pulse to a prescribed imaging slice to suppress MR signals in the prescribed imaging slice;

b) controlling the RF system and gradient coils to apply an RF saturation pulse to a prescribed volume that is outside of the prescribed imaging slice to suppress MR signals indicative of venous blood that flows into the prescribed imaging slice;

c) observing a quiescent inflow time period (QITP) at least equal to half a projected duration of a cardiac cycle of the subject;

d) controlling the RF system and gradient coils to apply an RF excitation pulse to the prescribed imaging slice;

e) acquiring k-space data from the prescribed imaging slice as a plurality of projections in which a time delay (TR) between sequential projections is selected to allow a random distribution of flow-induced phase shifts to accumulate throughout k-space to control signal loss and artifact-inducing components in the k-space data without synchronization to the cardiac cycle; and f) reconstructing, from the acquired k-space data, an image of the subject including at least the prescribed imaging slice.

18. The method of claim 17 wherein in each projection and respective adjacent projections in the plurality of projections are non-adjacent projections in k-space.

19. The method of claim 17 wherein each projection in the plurality of projections extends through a center of k-space.

20. The method of claim 17 wherein step f) further comprises analyzing each of the plurality of projections to identify projections acquired during periods in the cardiac cycle causing at least one of rapid and accelerating blood flow and discarding identified projections prior to reconstructing the image of the subject.

21. The method of claim 17 wherein step f) includes using a maximum intensity projection algorithm to reconstruct the image of the subject.

* * * * *